(12) United States Patent
Mistretta et al.

(10) Patent No.: US 7,218,702 B2
(45) Date of Patent: May 15, 2007

(54) X-RAY SYSTEM FOR USE IN IMAGE GUIDED PROCEDURES

(75) Inventors: Charles Anthony Mistretta, Madison, WI (US); Howard Andrew Rowley, Madison, WI (US); Michael Scott VanLysel, Madison, WI (US); Guang-Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 520 days.

(21) Appl. No.: 10/842,181

(22) Filed: May 10, 2004

(65) Prior Publication Data

US 2005/0251010 A1 Nov. 10, 2005

(51) Int. Cl.
*A61B 6/02* (2006.01)

(52) U.S. Cl. .............................. 378/21; 378/22; 378/27; 378/98.12; 382/130; 382/131

(58) Field of Classification Search .................... 378/4, 378/21, 22, 27, 98.11, 98.12; 382/128, 130, 382/131
See application file for complete search history.

(56) References Cited

U.S. PATENT DOCUMENTS

| | | | |
|---|---|---|---|
| 4,903,204 A | 2/1990 | Dobbins, III | |
| 5,278,884 A | 1/1994 | Eberhard et al. | |
| 6,196,715 B1* | 3/2001 | Nambu et al. | 378/197 |
| 2002/0168053 A1 | 11/2002 | Schomberg | |
| 2007/0010731 A1* | 1/2007 | Mistretta | 600/407 |

FOREIGN PATENT DOCUMENTS

EP 1 302 163 A2 10/2002

OTHER PUBLICATIONS

Guang-Hong Chen, An Alternative Derivation Of Katsevich's Cone-Beam Reconstruction Formula, Med. Phys. vol. 30, No. 12, Dec. 2003, pp. 3217-3226.
James T Dobbins III & Devon J Godfrey, Digital X-ray Tomosynthesis: current state of the art and clinical potential,Phys. Med. Biol. 49 (2003) R65-R106.
H. Schmitt, et al, An X-ray Based Method for the Determination of the Contrast Agent Propagation in 3-D Vessel Structures, IEEE Trans. on Med Imaging., vol. 21, No. 3, Mar. 2002, pp. 251-262.
Simon D. Shpilfoygel et al, X-ray videodensitometric methods for blood flow and velocity measurement: A critical review of literature, Med. Phys. 27(9), Sep. 2000 pp. 2008-2023.

* cited by examiner

*Primary Examiner*—Edward J. Glick
*Assistant Examiner*—Chih-Cheng Glen Kao
(74) *Attorney, Agent, or Firm*—Quarles & Brady LLP

(57) ABSTRACT

An x-ray system for use with image-guided medical procedures is programmed to move in a first scan path to acquire cone beam attenuation data from which a three-dimensional digital subtraction angiogram of selected vasculature is reconstructed. The x-ray system is also programmed to move in a second scan path to acquire a series of tomosynthesis images during the inflow of a contrast agent into the selected vasculature. Parametric images are produced from information in the tomosynthesis images which indicate blood perfusion physiology of the tissues served by the vasculature.

16 Claims, 7 Drawing Sheets

X-RAY SYSTEM FOR USE IN IMAGE GUIDED PROCEDURES

This invention was made with government support under Grant No. HL66488 awarded by the National Institute of Health. The United States Government has certain rights in this invention.

BACKGROUND OF THE INVENTION

The field of the invention is medical imaging and particularly the acquisition of x-ray images for use in image-guided medical procedures.

Stroke afflicts more than 700,000 people yearly in the United States alone. Approximately 85 percent of strokes are caused by an ischemic mechanism, either from local thrombosis or clot embolism. The only FDA-approved method for clinical treatment of acute ischemic stroke is a thrombolytic agent, tissue plasminogen activator (tPA), started intravenously within 3 hours of stroke onset. Patients are selected for tPA treatment based on clinical features and basic non-contrast CT (computed tomography) imaging criteria, with the exact site of clot not directly confirmed in most instances.

Following the clinical trials which lead to tPA approval, subsequent real-world use in many centers has confirmed improved outcomes in patients treated with tPA. However, initial enthusiasm for thrombolysis has declined to more cautious and limited deployment in most centers. Limitations of IV injected tPA include the short time window available to identify and treat patients, controversies on how to select candidates for treatment, the relatively modest effectiveness and outcome benefit perceived by clinicians, and the rare but often fatal hemorrhages which occur as a complication. More than five years after introduction of the drug, fewer than 2 percent of acute stroke patients are treated with tPA.

Recent trials have demonstrated that the 3 hour time window in which the benefits of tPA outweigh its risks can be lengthened. During a 2 hour period, pro-urokinase was infused and angiographic images were acquired to monitor clot lysis and assess blood flow. Even as late as 6 hours after stroke symptom onset, high rates of clot lysis can be achieved. Clinical outcome in these cases often is determined by the residual perfusion of affected tissues rather than the state of clot lysis as seen in conventional angiograms. Thus, the acquisition of perfusion images of the affected tissues is an important tool in assessing the advisability of using tPA treatment.

Contrast techniques can be used with multi-slice x-ray CT to provide perfusion parameter maps. Such perfusion images are acquired after the injection of a contrast agent using an x-ray CT system. The acquisition of such images and the assessment of brain perfusion and its relationship to infarcted areas has become central to advanced clinical techniques and the making of decisions regarding patient selection for acute treatments. Perfusion assessment brings an individual, patient-specific physiologic-based method (not just time or anatomy) to select candidates who are most likely to benefit, while simultaneously excluding patients who could be hurt by these potentially risky treatments.

While it has become evident that perfusion measurement is important in acute stroke, none of the current imaging methods can be performed directly in the angiographic suite where intra-arterial thrombolysis is conducted. MR and CT-based perfusion methods have shown value, but must be done before or after the interventional angiographic procedure itself. Other traditional perfusion techniques using PET, SPECT, or XeCT have also been used for acute stroke, but are more lengthy procedures, have not seen widespread practical utility, and cannot be performed during the angiographic procedure.

Some medical centers have combined angiography-MRI facilities ("XMR") to offer interventional angiography-perfusion/diffusion capability, but these facilities still require moving an acutely ill patient from one imaging room to another to conduct interventional angiography and perfusion assessment in an interleaved fashion. All these current approaches are inefficient and require moving a patient who may be at risk of bleeding due to drugs and indwelling intra-arterial catheters.

SUMMARY OF THE INVENTION

The present invention is an x-ray imaging system that may be used for image-guided medical procedures which includes: an x-ray source; an x-ray detector; a drive mechanism for moving the x-ray source and x-ray detector about a subject positioned therebetween in a programmed path; a first stored program for moving the x-ray source and x-ray detector along a first path and acquiring a first data set from which an angiogram that depicts vasculature in the subject is reconstructed and displayed; and a second stored program for moving the x-ray source and x-ray detector along a second path and acquiring a second data set from which an image indicative of blood perfusion in tissue in the subject is reconstructed and displayed.

In a preferred embodiment of the invention the x-ray imaging system provides cone beam volume computed tomography (VCT) digital subtraction angiography (DSA) capability and tomosynthetic DSA perfusion capability in a C-arm vascular interventional imaging system. It provides improved 3D anatomical imaging with isotropic image voxels as well as time-resolved tomographic information on contrast dynamics. This information is useful in guiding therapy, planning surgical procedures, and evaluating interventions in a number of clinical applications.

A general object of the invention is to provide a single imaging system that can be used to acquire and display angiograms that depict the vasculature of the subject and to acquire and display parametric images that indicate perfusion of tissues. The angiograms provide the physician with anatomic information concerning the integrity of the subject's vasculature system, and the parametric images provide physiological information concerning the perfusion of tissues served by the vasculature. This information improves the efficacy of minimally invasive medical procedures and reduces the morbidity of such procedures.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1A:
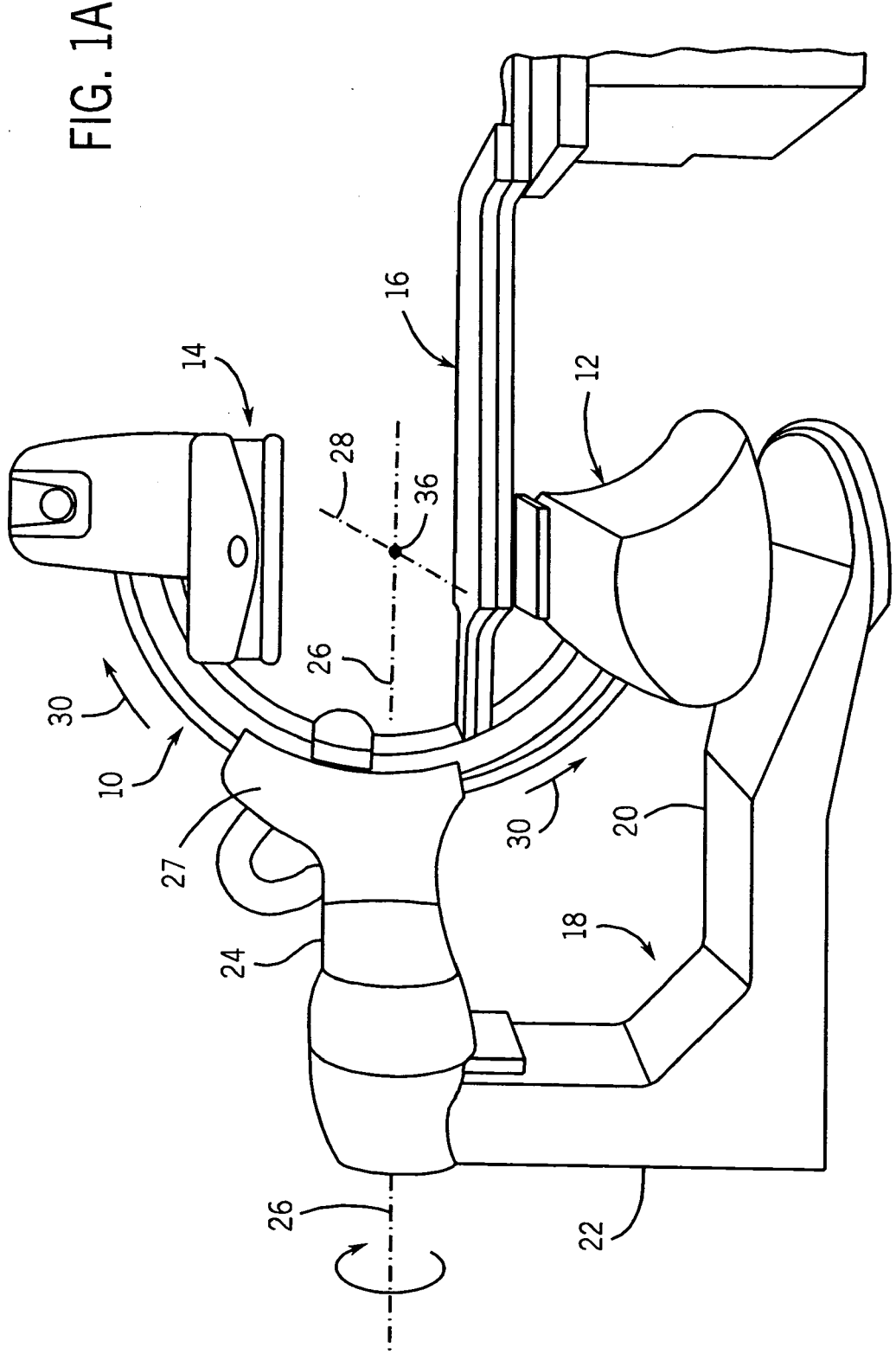
FIGS. 1A and 1B are perspective views of an x-ray system which employs a preferred embodiment of the present invention.
Figure 1B:
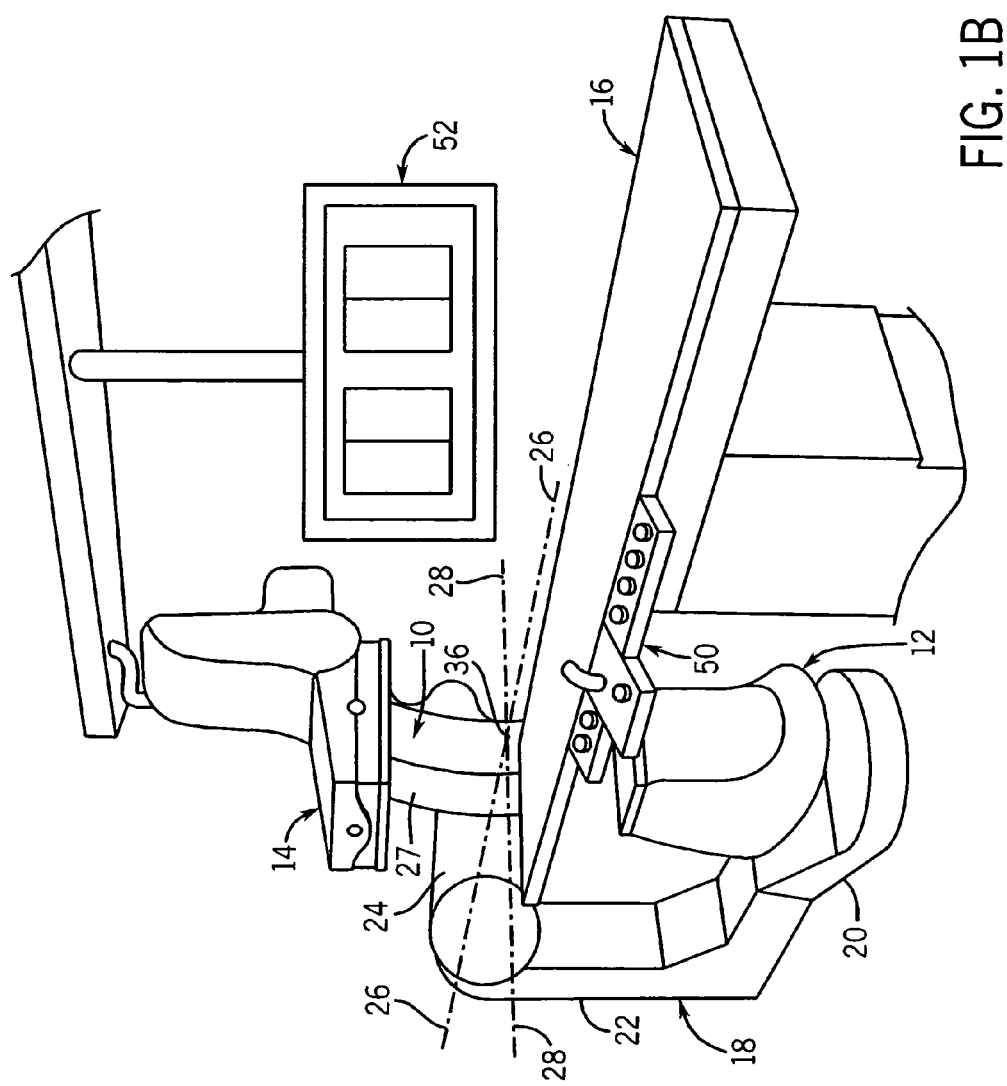
Figure 2:
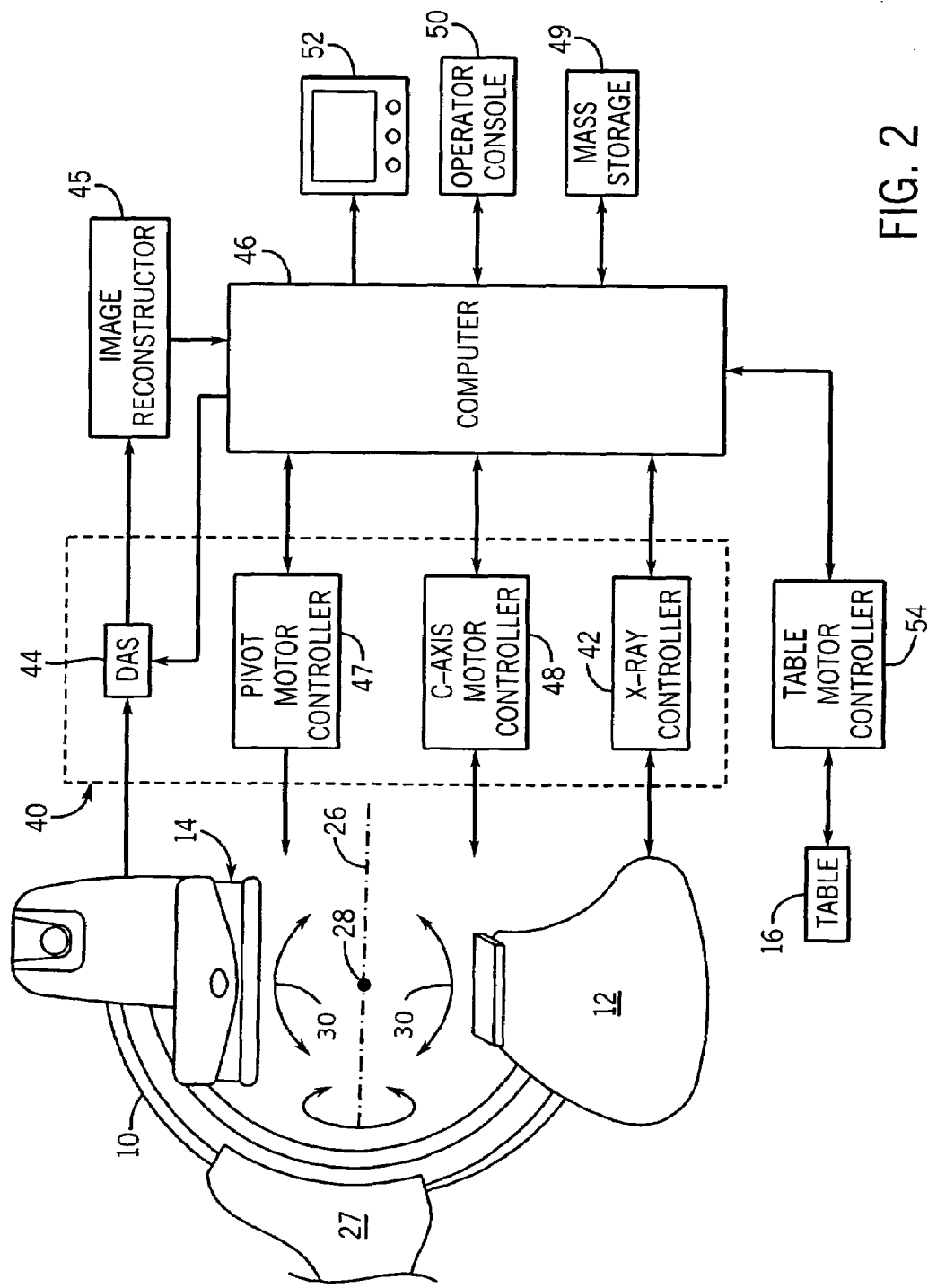
FIG. 2 is a schematic block diagram of the x-ray system of FIG. 1.

Referring particularly to FIGS. 1 and 2, the preferred embodiment of the invention employs an x-ray system that is designed specifically for use in connection with interventional procedures. It is characterized by a gantry having a C-arm 10 which carries an x-ray source assembly 12 on one of its ends and an x-ray detector array assembly 14 at its other end. The gantry enables the x-ray source 12 and detector 14 to be oriented in different positions and angles around a patient disposed on a table 16, while enabling a physician access to the patient.

The gantry includes an L-shaped pedestal 18 which has a horizontal leg 20 that extends beneath the table 16 and a vertical leg 22 that extends upward at the end of the horizontal leg 20 that is spaced from of the table 16. A support arm 24 is rotatably fastened to the upper end of vertical leg 22 for rotation about a horizontal pivot axis 26. The pivot axis 26 is aligned with the centerline of the table 16 and the arm 24 extends radially outward from the pivot axis 26 to support a C-arm drive assembly 27 on its outer end. The C-arm 10 is slidably fastened to the drive assembly 27 and is coupled to a drive motor (not shown) which slides the C-arm 10 to revolve it about a C-axis 28 as indicated by arrows 30. The pivot axis 26 and C-axis 28 intersect each other at an isocenter 36 located above the table 16 and they are perpendicular to each other.

The x-ray source assembly 12 is mounted to one end of the C-arm 10 and the detector array assembly 14 is mounted to its other end. As will be discussed in more detail below, the x-ray source 12 emits a cone beam of x-rays which are directed at the detector array 14. Both assemblies 12 and 14 extend radially inward to the pivot axis 26 such that the center ray of this cone beam passes through the system isocenter 36. The center ray of the cone beam can thus be rotated about the system isocenter around either the pivot axis 26 or the C-axis 28, or both during the acquisition of x-ray attenuation data from a subject placed on the table 16.

Figure 3:
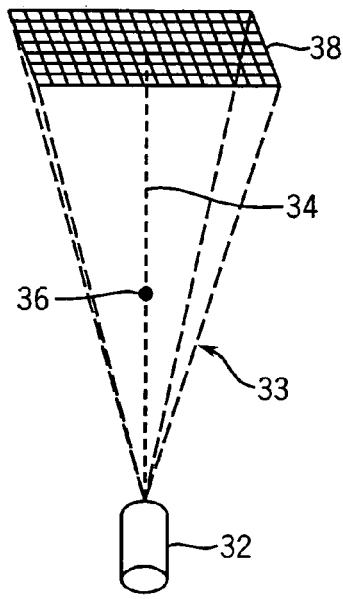
FIG. 3 is a pictorial view of an x-ray source and detector array which forms part of the x-ray system of FIG. 1.

As shown in FIG. 3, the x-ray source assembly 12 contains an x-ray source 32 which emits a cone beam 33 of x-rays when energized. The center ray 34 passes through the system isocenter 36 and impinges on a two-dimensional flat panel digital detector 38 housed in the detector assembly 14. The detector 38 is a 2048 by 2048 element two-dimensional array of detector elements having a size of 41 cm by 41 cm. Each element produces an electrical signal that represents the intensity of an impinging x-ray and hence the attenuation of the x-ray as it passes through the patient. During a scan the x-ray source 32 and detector array 38 are rotated about the system isocenter 36 to acquire x-ray attenuation projection data from different angles. The detector array is able to acquire 30 projections, or views, per second and this is the limiting factor that determines how many views can be acquired for a prescribed scan path and speed.

Referring particularly to FIG. 2, the rotation of the assemblies 12 and 14 and the operation of the x-ray source 32 are governed by a control mechanism 40 of the CT system. The control mechanism 40 includes an x-ray controller 42 that provides power and timing signals to the x-ray source 32. A data acquisition system (DAS) 44 in the control mechanism 40 samples data from detector elements 38 and passes the data to an image reconstructor 45. The image reconstructor 45, receives digitized x-ray data from the DAS 44 and performs high speed image reconstruction according to the methods of the present invention. The reconstructed image is applied as an input to a computer 46 which stores the image in a mass storage device 49 or processes the image further to produce parametric images according to the teachings of the present invention.

The control mechanism 40 also includes pivot motor controller 47 and a C-axis motor controller 48. In response to motion commands from the computer 46 the motor controllers 47 and 48 provide power to motors in the x-ray system that produce the rotations about respective pivot axis 26 and C-axis 28. As will be discussed below, a program executed by the computer 46 generates motion commands to the motor drives 47 and 48 to move the assemblies 12 and 14 in a prescribed scan path.

The computer 46 also receives commands and scanning parameters from an operator via console 50 that has a keyboard and other manually operable controls. An associated cathode ray tube display 52 allows the operator to observe the reconstructed image and other data from the computer 46. The operator supplied commands are used by the computer 46 under the direction of stored programs to provide control signals and information to the DAS 44, the x-ray controller 42 and the motor controllers 47 and 48. In addition, computer 46 operates a table motor controller 54 which controls the motorized table 16 to position the patient with respect to the system isocenter 36.

The computer 46 stores programs which enable it to perform two very different scans. The first scan acquires three-dimensional attenuation data and produces an angiogram which depicts the anatomic structure of the subject's vasculature. A three-dimensional image is acquired before injection of a contrast agent and a three-dimensional image is acquired after the contrast agent flows into the vasculature of interest. The two images are subtracted and the resulting 3D difference image may be projected at any angle to produce a 2D angiogram. This scan is called a volume CT digital subtraction angiogram and is referred to herein as "VCT DSA".

The second scan performed by programs stored in the computer 46 produces images from which physiological information can be extracted to indicate the perfusion of blood into tissues. A first reference image is acquired prior to contrast injection using a tomosynthesis method and then a series of tomosynthesis images are acquired at one second intervals as the contrast agent flows into the region of interest. After subtraction of the reference image, these tomosynthesis images are used to calculate regional blood flow (rBF), regional blood volume (rBV) and regional mean transit time (rMTT) and produce corresponding parametric images. This scan employs tomosynthetic digital subtraction angiography and is referred to herein as "TDSA".

Under the direction of a physician who is operating the x-ray system through the operator console 50, a patient is positioned on the table 16 and the region of interest is moved to the system isocenter 36 by manipulating the table 16. The VCT DSA scan is then performed and the resulting angiogram produced on the display 52. This image is anatomical and indicates the structure of blood vessels in the region of interest. Without moving the patient, the physician may then initiate the TDSA scan. This results in images indicating the physiology of tissues in the region of interest, and in particular the perfusion of blood to those tissues. Armed with this information, the physician is then able to make an informed decision regarding the interventional procedure at hand. For example, a decision might be made to inject a thrombolytic agent into the patient because there are significant "at risk" tissues which can still be saved if blood flow is returned to them.

VCTDSA Image Acquisition

Figure 4:
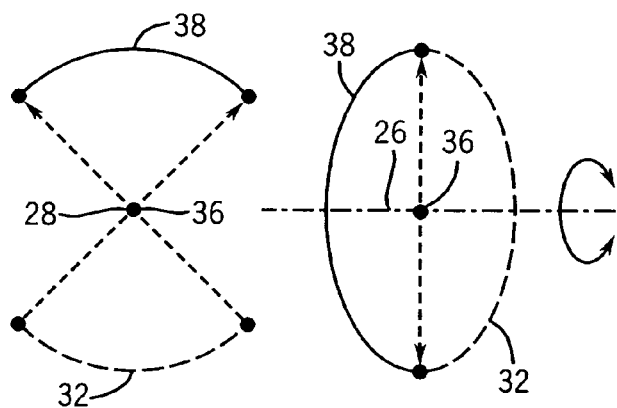
FIG. 4 is a pictorial representation of a first scan path performed by the x-ray system of FIG. 1 to acquire x-ray attenuation data.
Figure 6:
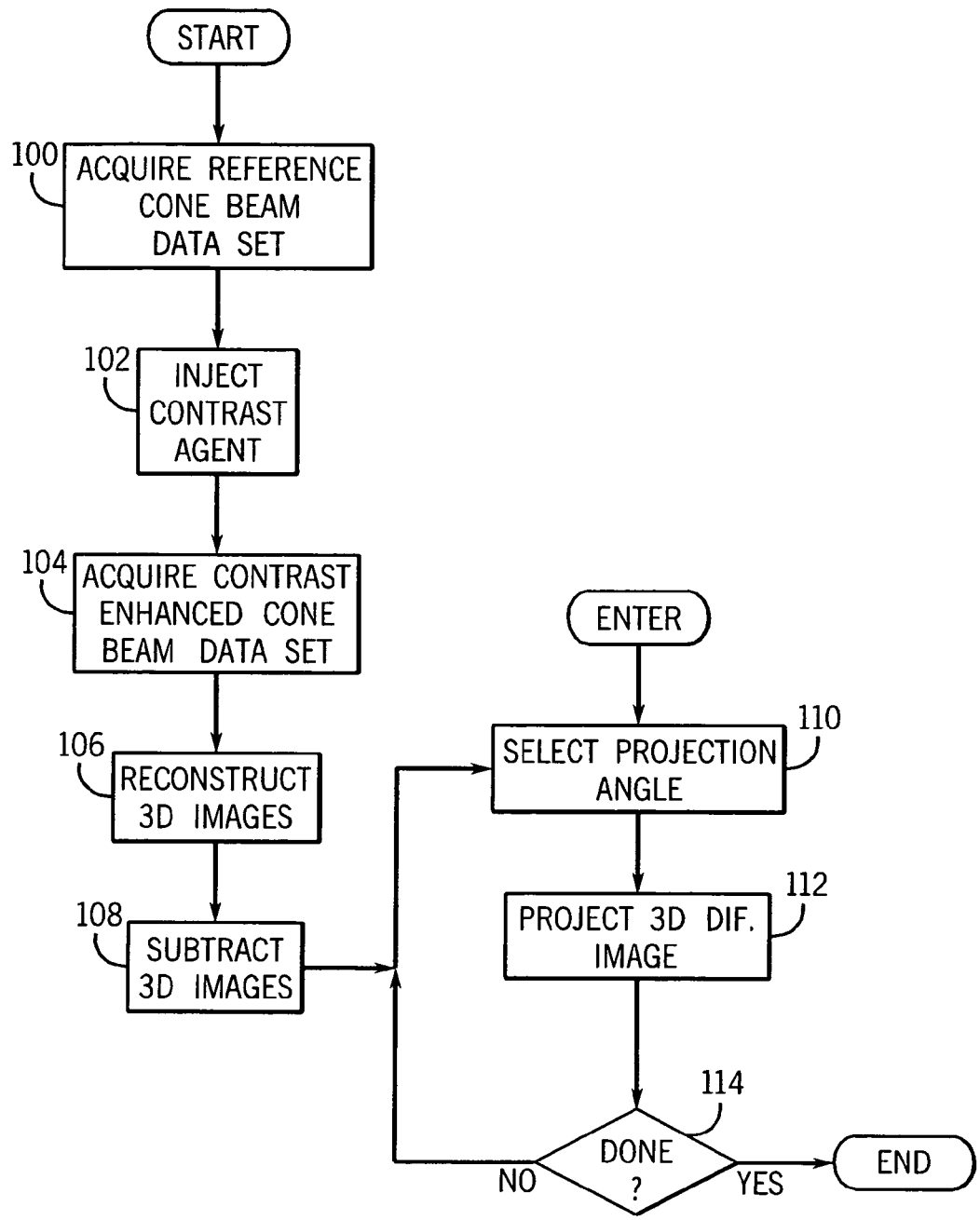
FIG. 6 is a flow chart which illustrates the steps performed by the x-ray system of FIG. 1 to produce a 3D anatomical image from attenuation data acquired with the first scan path of FIG. 4.

Referring particularly to FIG. 6, when the VCTDSA scan is performed the gantry is moved in a first prescribed path to acquire a reference cone beam data set as indicated at process block 100. The objective is to acquire sufficient attenuation projection views of the three-dimensional region of interest such that an artifact free three-dimensional image can be reconstructed. As shown in FIG. 4, this first scan path is comprised of two parts. First, a set of 90 views are acquired as the x-ray source 32 and detector array 38 are revolved in a 90° arc around the C-axis 28. Then, the x-ray source 32 and detector array 38 are revolved around the pivot axis 26 to acquire 180 views over a 180° arc. This first scan path is thus comprised of two circular arcs disposed in perpendicular planes. The acquired projections are stored as a reference cone beam data set.

Referring again to FIG. 6, the next step is to inject a contrast agent into the subject as indicated at process block 102. This can be performed either intravenously or intra-arterially. After the contrast agent flows into the region of interest another cone beam data set is acquired as indicated at process block 104. This acquisition is performed as described above and the only difference between the resulting cone beam data set and the previously acquired reference cone beam data set is that attenuation values are different due to the presence of contrast agent in the vasculature of interest.

As indicated at process block 106, the next step is to reconstruct two 3D images from the two cone beam data sets. There are a number of methods for doing this, but as will be described below in detail, we have discovered a novel image reconstruction method for this particular clinical application. A 3D difference image is then calculated at process block 108 by subtracting the reference 3D image from the contrast enhanced 3D image. The resulting 3D difference image is displayed for the physician who can rotate the vascular structures depicted on the display to obtain the best view of the region of interest. As indicated at process block 110, when a desirable viewing angle is found it is selected and a 2D sliced image is produced as indicated at process block 112. The physician can select additional sliced images and produce corresponding 2D images until all the viewing angles of interest have been examined as indicated at decision block 114. The 3D difference image enables the anatomical structure of the vascular tree in the region of interest to be examined from any angle.

VCTDSA Image Reconstruction

There are three difficulties commonly encountered when reconstructing 3D images from cone beam data sets. First, artifacts will be produced in the 3D image if the cone-beam projection data is not acquired from an appropriate design of the x-ray source orbit. This is a geometric problem of not acquiring views from a sufficient number of angles and is common to cone beam acquisitions with conventional CT systems that employ a single circular acquisition path. This data sufficiency problem is solved in the preferred embodiment of the present invention by acquiring cone beam projection data along a scan path comprised of two circular arcs disposed in perpendicular planes.

A second difficulty is the inability to acquire enough views in a specified time frame to satisfy the Nyquist criteria. This is called undersampling and the commonly believed consequence of undersampling within the prescribed scan path is streak artifacts in the reconstructed image. Most of the streak artifacts are static and are common to both the reference and contrast-enhanced images. We have discovered that undersampling by up to a factor of 50 is possible without producing clinically significant artifacts if a reference image is subtracted from the contrast enhanced image and if the images are isotropic 3D images which spread artifacts out in three dimensions rather than two. Streak artifacts common to both images are removed from the final difference image. As a result, good 3D images can be produced with as few as 300 to 400 views of cone beam data.

A final difficulty with cone beam reconstruction methods is that the rays are divergent instead of parallel. The conventional projection-slice theorem establishes a bridge between the Fourier transform of parallel beam x-ray projections and a slice of the Fourier transform of an image object. In other words, a complete Fourier space of the image object can be constructed from a superposition of the Fourier transform of the parallel beam projections. After the complete Fourier space of the image object is constructed, an inverse Fourier transform can be performed to reconstruct the image of the object. However, this is not valid for divergent rays produced in a cone beam. Various methods have been proposed to approximate the reconstructed image based on parallel beam principles. We have developed a new cone beam reconstruction method which provides an exact reconstructed image from the cone beam data set.

The parallel beam projection-slice theorem tells us how each individual view of projections contributes to Fourier space of an image object. Namely, Fourier space of the image object is constructed from the Fourier transform of the back-projection of the parallel beam projections. In the parallel beam case, the image object is spatially shift-invariant in an individual view of projections. Therefore, it is natural to equally weigh the data during the back-projection. In other words, the detected x-ray attenuation data will be put back uniformly to every point along the projection direction. Thus, the Fourier transform of the back-projected data array only generates non-zero Fourier components in a plane perpendicular to the projections. Namely, a slice in Fourier space is generated by the Fourier transform of the projection data.

However, for the divergent beam projections, the equal weighting scheme is not appropriate because of the diverging nature of the beam. We have found that a proper weighting scheme is to multiply the measured data by a distance-dependent pre-weighting factor $$\frac{1}{r},$$

where r is the distance from the x-ray source position to the back-projected point. After this pre-weighted back-projection step, the 2D projections become a fully 3D non-uniform data array within a cone. We take the Fourier transform of this weighted back-projection data array. A local Fourier space can be generated with the center of the Fourier space at the x-ray source location. In the cone beam case, this local Fourier transform is written as:

$$G_3[\hat{k}, \vec{y}(t)] = \int_R \int_3 \int d^3 r \left[\frac{1}{r} \times g(\hat{r}, \vec{y}(t))\right] e^{i2\pi \hat{k} \cdot \vec{r}}$$
$$= \int_0^\infty dl l \tilde{f}(l, \hat{k}) e^{i2\pi l \hat{k} \cdot \vec{y}(t)}$$

In the first line, the $$\frac{1}{r}$$

weighting on the acquired cone beam data g [$\hat{r}$, $\vec{y}$(t)] has been highlighted in the square bracket. The vector $\vec{y}$(t) is used to label the x-ray tube position (focal spot). A hat is used to denote a unit vector and an arrow is used to denote a general vector. The second line of the above equation illustrates the relation between the Fourier transform of an image object $\tilde{f}$(l, $\hat{k}$) and the Fourier transform of the $$\frac{1}{r}$$

pre-weighted cone beam projections. We rebin the above partial Fourier transform data by introducing a new variable p:

$$p = \hat{k} \cdot \vec{y}(t)$$

Then the above equation is transformed into:

$$G_3(p, \hat{k}) = \int_0^\infty dl l \tilde{f}(l, \hat{k}) e^{i2\pi l p}$$

For each of the projections, this procedure is repeated. For a specific Fourier space orientation $\hat{k}$, there may be more than one focal spot corresponding to the same p value. This represents the data redundancy in the divergent beam data acquisitions. Since each projection has generated an individual Fourier space around the x-ray source position, all local Fourier transforms are shifted to one fixed laboratory location. According to the shift theorem of the Fourier transform, this step requires an extra phase factor. After shifting, all the intermediate results are summed to obtain the desired Fourier transform of the target image object. Mathematically, this amounts to performing an inverse Laplace-Fourier transform to obtain the Fourier transform $\tilde{f}$(k,$\hat{k}$) from rebinned data $G_3$(p,$\hat{k}$):

$$\tilde{f}(k, \hat{k}) = \frac{1}{2\pi k^2} \int dp \cos(2\pi kp) \frac{d}{dp} \text{Im} G_3(p, \hat{k})$$

The integral is over all the possible rebinned p values. The symbol Im means the imaginary part.

The numerical implementation can be illustrated by the following pseudo code:

Step 1: for each acquired view t, calculate $G_3$($\hat{k}$, $\vec{y}$(t))
Step 2: rebin data to $G_3$(p,$\hat{k}$) by p=$\hat{k}$·$\vec{y}$(t)
Step 3: calculate $\tilde{f}$(k,$\hat{k}$) by using $G_3$(p,$\hat{k}$).

After these three steps, the physically measured cone beam projection data has been transformed into the Fourier space (i.e., k-space) version of the target image object. The 3D image of the object is then produced by Fourier transforming this k-space data.

There are alternative methods for reconstructing 3D images from acquired cone beam data sets. Two of these are described by:

Katsevich A. "A General Scheme For Constructing Inversion Algorithms For Cone Beam CT", Int. J. Math and Math SCI. 2003; 21, 1305–1321; and Chen G H. "An Alternative Derivation Of Katsevich's Cone-Beam Reconstruction Formula", Med. Phys. 2003; 30.

These are generalized methods for use with cone beam data acquired with any scan path. Either of these generalized methods can be used by solving their general formula for the particular double-arc scan path used herein.

TDSA Image Acquisition

Figure 5:
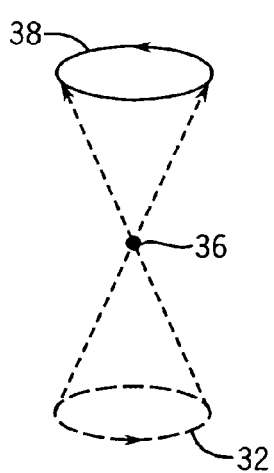
FIG. 5 is a pictorial representation of a second path performed by the x-ray system of FIG. 1 to acquire x-ray attenuation data.
Figure 7:
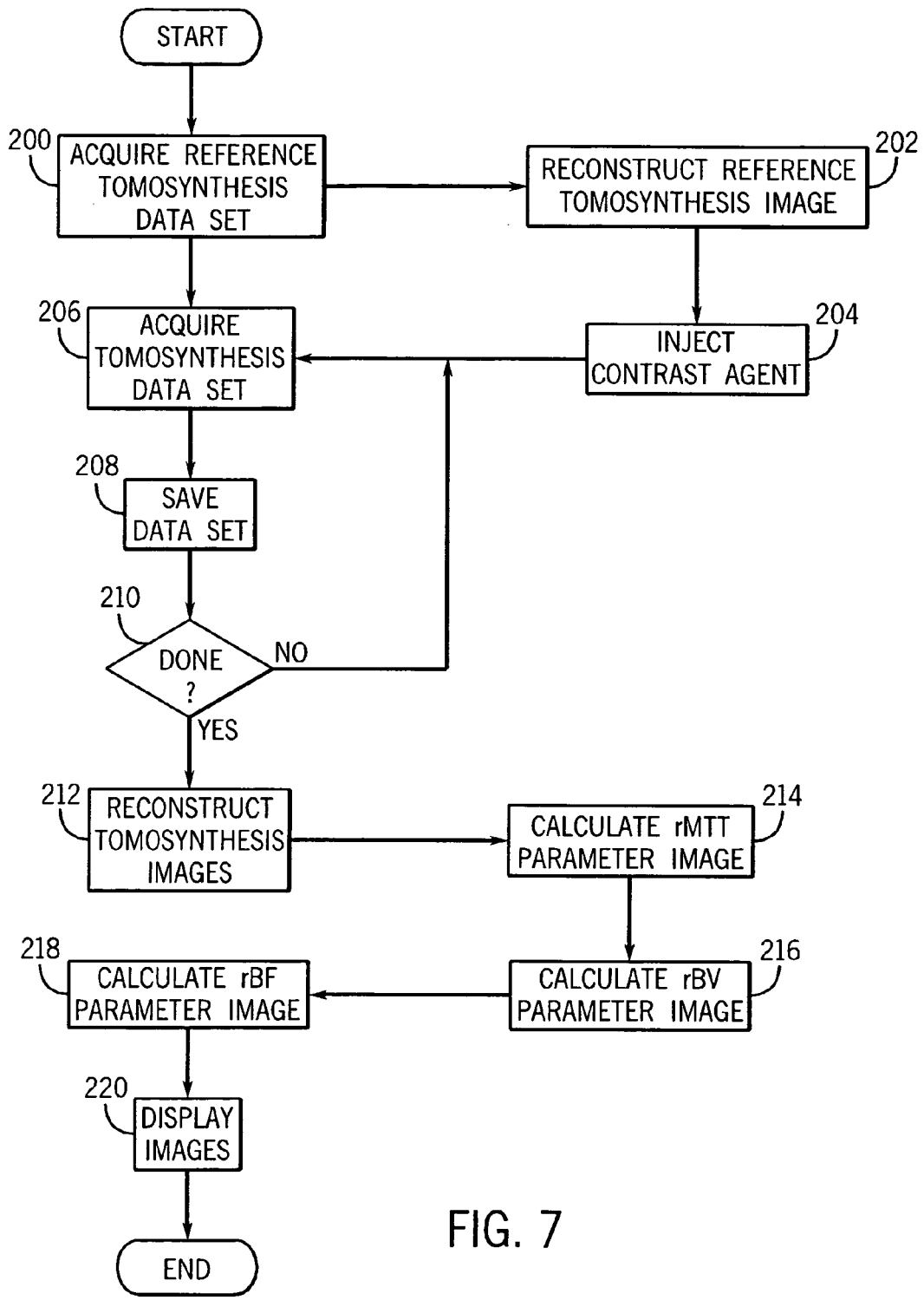
FIG. 7 is a flow chart which illustrates the steps performed by the x-ray system of FIG. 1 to produce parametric images from the attenuation data acquired with the second scan path of FIG. 5.

Referring particularly to FIG. 7, when the TDSA scan is performed the gantry is moved in a second prescribed path to acquire a reference tomosynthesis data set as indicated at process block 200. As shown in FIG. 5, this second scan path is performed by simultaneously operating the pivot axis motor controller 47 and C-axis motor controller 48 to move the x-ray source 32 in a circular or elliptical orbit below the isocenter 36 and the detector 38 in a corresponding circular orbit above the isocenter 36. The size of the circular orbit is determined by a number of factors, but the objective is to make the enclosed area of the path as large as possible. The constraining factor is that the gantry should move through the entire circular path to acquire a single tomosynthesis data set at the frame rate needed to capture the dynamic changes that occur during the inflow of contrast agent. In the preferred embodiment a frame rate of one image acquisition per second is prescribed and the gantry is capable of a circular path of 5 cm in diameter. Up to 10 tomosynthesis image data sets are acquired in this manner and corresponding views are averaged to form the reference tomosynthesis data set.

As indicated at process block 202, a reference tomosynthesis image is reconstructed from the acquired reference data set. Each acquired view in the reference data set is a radiograph acquired at a specific point on the circular scan path. A 2D image is formed by superimposing these views and translating them with respect to each other. The location of the 2D image plane is determined by the degree of translation and the 2D tomogram can thus be selectively located above or below the system isocenter 36. This reconstruction process is described in more detail below.

As indicated at process block 204, after acquisition of the reference tomosynthesis image the subject is injected with a contrast agent and a loop is entered in which a series of tomosynthesis data sets are acquired as the contrast flows into the region of interest. A manual common carotid injection of about 5 cc at an approximate rate of 5 cc/sec of 350 mg/cm$^3$ iodinated contrast solution is used. The x-ray source 32 and detector array 38 are continuously moved in the circular paths as shown in FIG. 5 and views are continuously acquired as indicated at process block 206. At the completion of each circular scan (approximately one second) the acquired views are saved as a tomosynthesis data set as indicated at process block 208. This data acquisition continues long enough to capture the entire tissue contrast enhancement curve, which can range from approximately 15 seconds to 60 seconds, depending on the location and rate of the injection, the region of interest and the type of pathological conditions present. The data acquisition phase is then complete as indicated at decision block 210, and each of the acquired tomosynthesis data sets are used to reconstruct corresponding images as indicated at process block 212.

While a circular scan path is employed in the preferred embodiment, other cyclical scan paths are possible. For example, if one axis of motion is faster than the other it can be operated at a higher speed to produce an elliptical scan path. The cyclical scan path is necessarily disposed to one side of the subject because it must be completely traversed at the desired frame rate. This means that the view angles that are acquired are limited in scope. This is a characteristic of tomosynthesis.

The reconstruction of the tomosynthesis images is the same as described above for the reference tomosynthesis image and then the reference tomosynthesis image is subtracted from each. The result is a series of difference tomosynthesis images which depict the inflow of blood into the arteries and tissues in the region of interest. This information is used to calculate a number of parameters which measure the blood perfusion in the tissues. Usually, the tomosynthesis images will be reconstructed at more than one plane so that blood perfusion can be assessed at different locations in the region of interest. Also, to make the parameter calculations an arterial contrast enhancement curve is needed and this requires tomosynthesis images in a plane that contains the artery that supplies the tissues of interest.

As indicated at process block 214, an image which depicts the regional mean transit time (rMTT) of blood flow into tissues is calculated by deconvolving tissue contrast enhancement curves and the arterial contrast enhance curve. As described in more detail below, both curves are obtained from the set, or sets, of tomosynthesis images. As indicated at process block 216, a regional blood flow volume (rBV) image is then calculated. As will be discussed below, the volume of flowing blood in a capillary network is calculated by the ratio of two areas under the tissue enhancement curve and arterial enhancement curve. And finally, a regional blood flow (rBF) image is calculated at process block 218. As will be described below, the blood flow information is derived from the rBV and rMTT information using the central volume principle.

At the completion of the scan the physician has three different parametric images of selected tissues. In most instances the same acquired data may be used to produce parametric images of all the tissues of interest. The acquired data may be used to reconstruct tomosynthesis images at different locations and the information therein may be used to produce the parametric images for tissues at those locations.

The multi-modal angiographic-perfusion imaging system has clinical application beyond acute stroke care. Perfusion data is helpful during endovascular management of cerebral vasospasm, in embolization of vascular malformations, and in determining the effects of stent placement or angioplasty on cerebral perfusion. Since some of these exams are done under general anesthesia and are complicated by blood pressure management problems, perfusion measurement helps guide the effectiveness of systemic pressor therapy. If an iatrogenic embolic complication was detected during an angiographic procedure, this technique is used to immediately assess the severity of any perfusion defect to help guide rescue interventions.

Interventional endovascular embolization therapies are increasingly used to treat both benign and malignant tumors throughout the body. Tumor treatment relates to both induced tumor ischemia and sometimes direct chemotherapy delivery, which targets the chemotherapeutic agent locally and also, slows its release from the tumor bed. Since procedural endpoints are not yet well established, direct perfusion measurements provide additional information to help guide the progress and extent of embolization. Brain meningiomas are highly vascular tumors which are commonly embolized through multiple feeding vessels, but the variable blood supply leads to a highly variable pattern of devascularization. With perfusion measurement, if parts of the tumor still show persistent perfusion after initial embolization, additional feeding vessels can be immediately sought and addressed to improve devascularization. In the case of liver tumors, either primary hepatocellular carcinomas or metastatic lesions (e.g., colorectal carcinoma) are commonly treated by transarterial chemoembolization. Perfusion measurements help establish the region and degree of parenchymal vascular stasis in both the hepatic artery and portal vein circulation. Likewise, uterine leiomyoma (fibroid) embolization may be tailored to take advantage of calibrated embolic agents and optimized to provide tumor stasis without causing the feared complication of uterine wall necrosis.

Parametric Image Reconstruction

This section describes the reconstruction of tomosynthesis images as discussed above with reference to process blocks 202 and 212, and the calculation of the parametric images from the tomosynthesis images as discussed above with reference to process blocks 214, 216 and 218.

The preferred method for reconstructing the tomosynthesis images is to use the preferred method described above for reconstructing the VCTDSA image. More specifically, the acquired cone-beam projection data is employed to calculate a k-space image of the object as set forth above in the three steps of pseudo code. An inverse Fourier transformation of this k-space image is then performed to produce an image of the subject. Of course, this method differs from the VCTDSA method in that the x-ray source paths are substantially different and the cone-beam projection data acquired using the tomosynthetic x-ray source path is not sufficient to reconstruct a complete k-space image of the subject. However, this method is preferred because k-space is at least uniformly filled and results in better quality tomosynthesis images despite the undersampling.

A first alternative method for reconstructing tomosynthesis images is to treat each acquired view of attenuation projection data as a projection radiograph. A tomosynthesis plane is selected through the subject and the views of acquired attenuation projection data are spatially translated with respect to each other and superimposed in such a manner that the images of structures in the tomosynthesis plane align exactly. The images of structures outside the tomosynthesis plane do not align exactly, resulting in a depth dependent blurring of these structures. By varying the amount of the relative translation of the projection radiographs, the location of the tomosynthesis plane can be varied within the object. Each time the tomosynthesis plane is varied, the image data corresponding to the overlapping structures is superimposed and a 2D image of the structure in the tomosynthesis plane is obtained. Many tomosynthesis methods are known in the art as exemplified by the method disclosed in U.S. Pat. No. 4,903,204, which issued on Feb. 20, 1990 and is entitled "Matrix Inversion Tomosynthesis Improvements In Longitudinal X-ray Slice Imaging," and which is incorporated herein by reference.

Another alternative method for reconstructing the tomosynthesis images is to treat each data set as a 3D cone beam data set and use one of the well known cone-beam reconstruction methods described above for the VCTDSA image reconstruction. Of course, the x-ray source path is totally different and the generalized cone beam reconstruction formulas must be solved for the second scan path used to acquire the tomosynthesis data sets. The result is a 3D image and any 2D slice of data may be selected for analysis.

Figure 8:
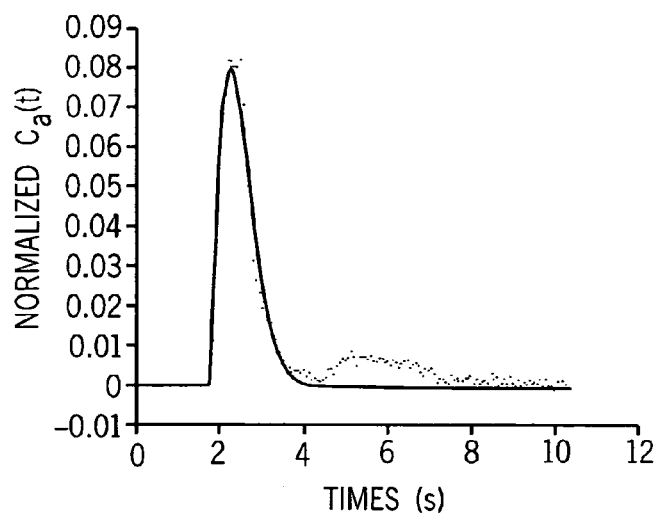
FIG. 8 is a graph of an exemplary arterial contrast enhancement curve produced during the procedure in FIG. 7
Figure 9:
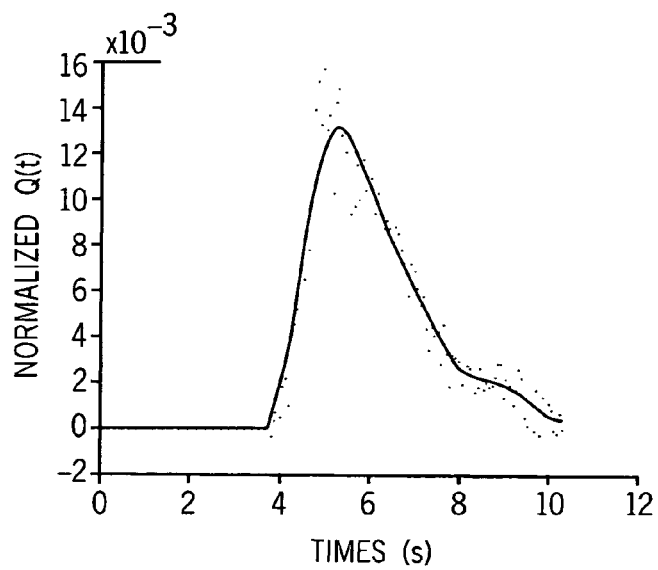
FIG. 9 is a graph of an exemplary tissue contrast enhancement curve produced during the procedure in FIG. 7.

The first step in calculating the parametric images from the reconstructed tomosynthesis images is to calculate an arterial contrast enhancement curve that indicates the increase in image intensity in an artery feeding the tissues of interest due to inflow of contrast agent. For this purpose pixels within the artery are selected and their intensity is plotted over the entire time series of images. It is preferable to select a plurality of pixels and average their values in each image frame. The arterial contrast enhancement curve is fit to these values with three 7 variant terms of similar form described by Yeung WIT, Lee T Y, Del Maestro R F, Kozak D, Bennett R J, Brown T, "An Absorptiometry Method For The Determination Of Arterial Blood Concentration Of Injected Iodinated Contrast Agent", Phys. Med. Biol. 1992; 37:1741–1758. An exemplary arterial contrast enhancement curve is shown in FIG. 8. This is compared with a typical tissue contrast enhancement curve shown in FIG. 9 generated by low pass filtering the average values of pixels depicting selected tissues served by the selected artery.

The measured tissue contrast enhancement curve or function, is actually a convolution of the arterial contrast enhancement curve, or input function, and an impulse function R(t). This is due to the fact that the bolus injection of contrast agent is not an instantaneous step function. This relation was quantified for constant cerebral blood flow (CBF) as:

$$Q(t) = CBF \times [C_a(t) \otimes R(t)]$$

by Meier P, Zierler K L. "On The Theory Of Indicator-dilution Method For Measurement Of Blood Flow And Volume", J. Appl. Physiol. 1954; 6:731–744.

Figure 10:
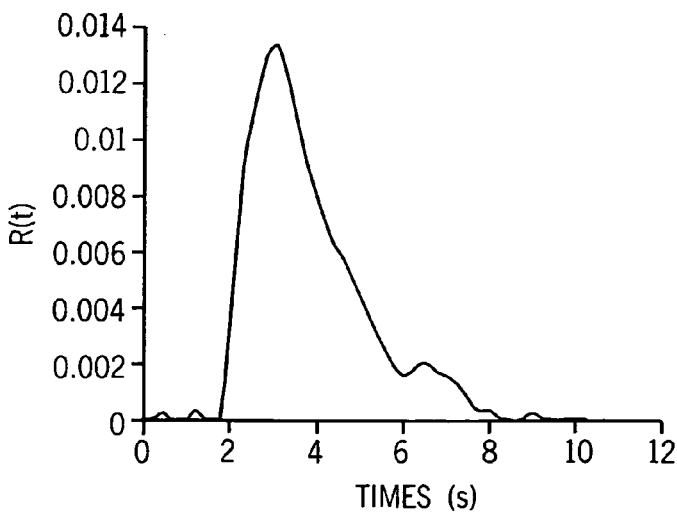
FIG. 10 is a graph of an exemplary impulse function curve produced during the procedure in FIG. 7.

The computation of the impulse function R(t) requires deconvolution of the tissue function and the arterial function, an operation which has a high sensitivity to noise. The Singular Value Decomposition (SVD) technique for deconvolution described in Press W H, Teukolsky S A, Vetterling W T, Flanney B T. "Numerical Recipes In C—The Art of Scientific Computing", $2^{nd}$ ed. Cambridge University Press, Oxford, 1992, is utilized. The resultant impulse function R(t) is illustrated in FIG. 10.

Once the impulse function R(t) is calculated, the regional Mean Transit Time (rMTT) perfusion parameter is calculated as follows:

$$rMTT = \frac{\text{area under } R(t)}{\text{height of } R(t)}.$$

The regional blood volume (rBV) perfusion parameter is calculated for the selected tissue by taking the ratio of the areas under the tissue contrast enhancement curve and the arterial contrast enhancement curve. This is described by Axel L. "Tissue Mean Transit Time From Dynamic Computed Tomography By A Simple Deconvolution Technique", Radiology 1980; 137: 679–686.

Using the central volume principle described by Meier P, Zierler K L. "On The Theory Of Indicator-dilution Method For Measurement Of Blood Flow And Volume", J. Appl. Physiol. 1954; 6:731–744, the regional blood flow (rBF) perfusion parameter is calculated next. This is accomplished by calculating the ratio of the regional blood volume (rBV) and the regional mean transit time (rMTT).

By repeating the above calculations at selected tissue locations separate perfusion parameter maps, or images, may be produced for each parameter rMTT, rBV and rBF. The parameter values can be displayed numerically at locations on an image of the region of interest, or parameter values can be used to modulate the color of pixels in an image of the region of interest.

The invention claimed is:

1. An x-ray system which comprises:
    an x-ray source;
    an x-ray detector;
    a drive mechanism for moving the x-ray source and x-ray detector in a programmed path about a subject positioned therebetween;
    a computer configured to operate in accordance with a first stored program for moving the x-ray source and x-ray detector along a first scan path to acquire a first data set and for reconstructing an angiogram that depicts vasculature in the subject from the first data set and in accordance with a second stored program for moving the x-ray source and x-ray detector along a second scan path to acquire a series of tomosynthesis data sets and for reconstructing a corresponding series of images depicting inflow of contrast agent into the vasculature and tissues served by the vasculature from the series of tomosynthesis data sets and wherein the computer is configured to operate in accordance with a third stored program for producing a parametric image from information in the series of images indicative of blood perfusion in tissues served by the vasculature; and
    a display coupled to the computer for receiving and displaying the angiogram and the parametric image.

2. The x-ray system as recited in claim 1 in which the parametric image indicates blood volume in the tissues.

3. The x-ray system as recited in claim 1 in which the parametric image indicates mean transit time.

4. The x-ray system as recited in claim 1 in which the parametric image indicates blood flow.

5. The x-ray system as recited in claim 1 in which the first scan path is comprised of a first arc disposed in a first plane that passes through the subject and a second arc disposed in a second plane that passes through the subject and is perpendicular to the first plane.

6. The x-ray system as recited in claim 1 in which the second scan path is a cyclic path disposed substantially to one side of the subject.

7. The x-ray system as recited in claim 6 in which the cyclic path is a circle.

8. The x-ray system as recited in claim 6 in which the cyclic path is an ellipse.

9. A method for producing an image with an x-ray system having an x-ray source which emits x-rays through a subject positioned in the x-ray system and an x-ray detector which receives the x-rays passing through the subject, the steps comprising:
   a) moving the x-ray source and x-ray detector along a first scan path to acquire a reference data set;
   b) moving the x-ray source and x-ray detector along a second scan path to acquire a reference tomosynthesis data set;
   c) injecting the subject with a contrast agent;
   d) moving the x-ray source and x-ray detector along said first scan path to acquire a contrast enhanced data set;
   e) moving the x-ray source and x-ray detector along said second scan path to acquire a tomosynthesis data set;
   f) repeating step e) to acquire a plurality of tomosynthesis data sets during in flow of contrast agent into vasculature of interest;
   g) producing an angiogram of the vasculature of interest by reconstructing two images from the respective reference data set and the contrast enhanced data set and subtracting the two images;
   h) reconstructing a reference tomosynthesis image from the acquired reference tomosynthesis data set;
   i) reconstructing a plurality of tomosynthesis images from the corresponding plurality of tomosynthesis data sets;
   j) calculating a blood perfusion parameter from said tomosynthesis images and tomosynthesis reference image; and
   k) displaying the blood perfusion parameter.

10. The method as recited in claim 9 in which the blood perfusion parameter is regional mean transit time (rMTT).

11. The method as recited in claim 9 in which the blood perfusion parameter is regional blood flow volume (rBV).

12. The method as recited in claim 9 in which the blood perfusion parameter is regional blood flow (rBF).

13. The method as recited in claim 9 in which the first scan path moves the x-ray source and x-ray detector along respective arcs to substantially opposite respective sides of the subject and in which the second scan path moves the x-ray source and x-ray detector along respective closed paths which are disposed on the opposite sides of the subject.

14. The method as recited in claim 9 in which the blood perfusion parameter is calculated at locations through a region of interest in the subject and blood perfusion parameter values are displayed on an image of the vasculature of interest.

15. The method as recited in claim 14 in which the image of the vasculature of interest is produced from the angiogram.

16. The method as recited in claim 15 in which the blood perfusion parameter values are displayed on the angiogram image by color modulating pixels therein.

* * * * *